US00PP27365P3

(12) United States Plant Patent
Austin

(10) Patent No.: US PP27,365 P3
(45) Date of Patent: Nov. 15, 2016

(54) ***ROSA HYBRIDA* SHRUB NAMED 'AUSMIXTURE'**

(50) Latin Name: *Rosa hybrida*
Varietal Denomination: AUSmixture

(71) Applicant: David Austin Roses Ltd., Albrighton, Wolverhampton (GB)

(72) Inventor: David J. C. Austin, Albrighton (GB)

(73) Assignee: David Austin Roses Ltd., Albrighton (GB)

( * ) Notice: Subject to any disclaimer, the term of this patent is extended or adjusted under 35 U.S.C. 154(b) by 15 days.

(21) Appl. No.: 14/545,309

(22) Filed: Apr. 20, 2015

(65) Prior Publication Data

US 2016/0050799 P1 Feb. 18, 2016

(51) Int. Cl.
*A01H 5/02* (2006.01)

(52) U.S. Cl.
USPC ..... Plt./107

(58) Field of Classification Search
USPC ..... Plt./107
CPC ..... A01H 5/0222
See application file for complete search history.

*Primary Examiner* — Kent L Bell
(74) *Attorney, Agent, or Firm* — KPPB LLP

(57) ABSTRACT

A variety of rose plant of the shrub class, named 'AUSmixture'. The 'AUSmixture' is a variety of a rose having cupped buds that gradually open to become large shallow-cupped fragrant rosettes of a soft pink with excellent disease resistance and vigor, and which repeat-flowers well.

1 Drawing Sheet

Classification: The present invention relates to a new *Rosa hybrida* shrub of the market class 'English Rose'.

Variety denomination: The new plant has the varietal denomination 'AUSmixture'.

CROSS-REFERENCE TO RELATED APPLICATION

The present application claims priority to European CPVO 2014/2047, filed Aug. 20, 2014.

ORIGIN OF INVENTION

This invention relates to a new and distinct variety of shrub rose plant named 'AUSmixture', which was originated from the cross-pollination of the two 'unnamed' and unpatented seedlings of *Rosa hybrida.*

BACKGROUND OF THE INVENTION

The primary objective of this breeding was to produce a rose variety having cupped buds that gradually open to become large shallow-cupped fragrant rosettes of a soft pink with excellent disease resistance and vigor, and which repeat-flowers well.

SUMMARY OF THE INVENTION

Among the features which distinguish the new variety from others presently available and commercial rose cultivars known to the inventor is the following combination of characteristics: vigorous, large shallow-cupped quartered rosettes having a soft shade of pink and a strong, fruity fragrance with excellent disease resistance and shiny foliage.

Asexual reproduction of the new variety by budding as performed at Bowling Green Lane in Albrighton, Britain shows that the foregoing and other distinguishing characteristics come true to form and are established and transmitted through succeeding asexual propagations. 'AUSmixture' may be asexually propagated by budding. The budding successfully occurred on the plant/rootstock *Rosa dumetorum* 'Laxa' for the observed plants.

COMPARISON WITH PARENTS

The seed and pollen parents of 'AUSmixture' are two unnamed seedlings. The new rose may be distinguished from its seed parent, by the following combination of characteristics: the seed parent is more disease prone and less free flowering, but with slightly fuller flowers. The new rose may be distinguished from its pollen parent, by the following combination of characteristics: the parent is apricot in color with blooms that have more of a hybrid-tea shaped flowers.

COMPARISON WITH THE CLOSEST COMMERCIALLY AVAILABLE CULTIVAR

The closest commercially available cultivar to the new variety is the 'AUSjosiah' (U.S. Plant Pat. No. 22,032) and 'AUSrumba' (U.S. Plant Pat. No. 17,500). The new rose may be distinguished from the 'AUSjosiah' variety by the following combination of characteristics: the 'AUSjosiah' has a bloom that is more rounded, whereas 'AUSmixture' has a cupped bloom. The blooms of 'AUSrumba' are apricot whereas the blooms of 'AUSmixture' are pink when the sepals are just dividing. In addition, neither 'AUSjosiah' nor 'AUSrumba' are quartered, and 'AUSmixture' is more compact with fewer thorns than the two commercially available cultivars.

BRIEF DESCRIPTION OF ILLUSTRATION

The accompanying photograph illustrates the new variety and shows the flowering thereof from bud to full bloom depicted in color as nearly correct as it is possible to make in a color illustration of the character.

Throughout this specification, color references and/or values are based upon The Colour Chart of The Royal Horticultural Society (2001) except where common terms of color definition are employed.

DESCRIPTION OF THE NEW VARIETY

Observations of budded 'AUSmixture' specimens were made in Albrighton, Wolverhampton, United Kingdom. The following description is of 5-year-old trial rose plants of the new variety grown in a garden environment in Albrighton, Britain in the month of June. Phenotypic expression may vary with environmental, cultural and climatic conditions, as well as differences in conditions of light and soil.

Flower characteristics:

*Blooming habit.*—Recurrent. The number of blooms per plant during the growing season is profuse, but there are too many to count.

*Bud.*—Size: About 3.5 cm long and 2 cm in diameter when the petals start to unfurl. Form: The bud form is blunt topped. Color: When sepals first divide, the bud color is RHS 63A (red-purple group). When half blown, the upper sides of the petals are RHS 65C (red-purple group), and the lower sides of the petals are RHS 65C (red-purple group). Calyx: Shape: star-shaped when the bloom is open and folds back against the stem. Length: 8 cm. Diameter: 8 cm. Sepals: Arrangement: Regularly arranged. Color: Upper Surface: green RHS 144B (yellow-green group). Lower Surface: green RHS 144A (yellow-green group) with RHS 181B (greyed-red group). Length: 3.5 cm. Width: 1.2 cm. Shape: Lanceolate. Surface texture: Upper Surface: Downy. Lower Surface: Slightly Glandular. Number: There are 3 normally appendaged sepals, and 2 unappendaged sepals with hairy edges. Receptacles: Color: RHS 144A (yellow-green group). Shape: funnel. Size: large, about 1.2 cm high×1.1 cm wide. Surface: Smooth. Peduncle: Length: medium, averaging about 8 cm. Surface: Rough. Color: RHS 144A (yellow-green group) with RHS 181A (greyed-red group). Strength: Strong.

*Blooms.*—Size: Large, average open diameter is about 9.5 cm. Borne: Several together in clusters of 5-8 with blooms having a rounded shape. Stems: Strength: Normal, average length is about 35-50 cm. Diameter: 5 mm. Form: When first open, bloom is cupped. Permanence of bloom: outer petals curl back.

*Petalage.*—Number of petals under normal conditions: 90. Color: The upper sides of the petals are RHS 65C (red-purple group). The reverse sides of the petals are RHS 65C (red-purple group). The base of the outer petals has a small yellow spot RHS 5C (yellow group). Variegations: None. Discoloration: The general tonality at the end of the first day is RHS 65C (red-purple group), and at the end of the third day is RHS 65C (red-purple group). Fragrance: Strong. Character of fragrance: fruity.

*Petals.*—Texture: Smooth. Size: Width: 35 mm. Length: 53 mm. Surface: Smooth. Shape: Obovate. Margin: Entire. Apex Shape: Rounded. Base Shape: Acute. Form: Incurved with some inner petals folded. Arrangement: Quartered. Petaloids: Number: Few 5-6. Color: RHS 65C (red-purple group). Length: 1-2 cm. Width: 4 mm-1 cm. Shape: Obovate, but narrow. Margin: Irregular. Persistence: Petals drop off cleanly before drying. Lastingness: On the plant: fair about 7 days. As a cut flower: not tested.

*Reproductive parts.*—Stamens: Number: around 62. Length: 8 mm. Anthers: Length: 1.5 mm. Color: RHS 15C (yellow-orange group). Arrangement: Regular around styles. Filaments: Color: RHS 15C (yellow-orange group). Length: 7 mm. Pollen: Color: RHS 15A (yellow-orange group). Pistils: Number: 40. Length: 8 mm. Styles: Color: RHS N155C (white group) with RHS 58B (red-purple group). Length: 7 mm. Stigmas: Color: RHS 22C (yellow-orange group). Length: 0.5-1 mm. Hips: None Observed.

Plant characteristics:

*Plant form.*—Shrub.

*Plant growth.*—Vigorous.

*Age to maturity.*—2 years.

*Mature plant.*—Height: 90 cm. Width: 75 cm.

*Rootstock.*—'Dr. Huey in the U.S. and *Rosa dumetorum* 'Laxa' for the observed plants in the UK.

*Foliage.*—Number: Leaflets on normal mid-stem leaves is: 5 (including terminal leaflet). Size: Large, about 17 cm long×14 cm wide. Quantity: Abundant. Number of leaves per flowering stem is: 7. Color: New foliage: Upper side: RHS 183A (greyed-purple group) with RHS 146A (yellow-green group). Lower side: RHS 183A (greyed-purple group) with RHS 146A (yellow-green group). Old foliage: Upper side: RHS 147A (yellow-green group). Lower side: RHS 146A (yellow-green group).

*Leaflets.*—Size: About 6.5 cm long×5 cm wide. Shape: Pointed oval. Base Shape: Rounded. Apex Shape: Acuminate. Texture: Leathery. Edge: Serrated. Serrations: Single. Petiole: Color: RHS 147A (yellow-green group) with RHS 183A (greyed-purple group). Length: 5 cm. Width: 2 mm. Surface Texture: Glandular. Petiole Rachis: Color: RHS 147A (yellow-green group) with RHS 183A (greyed-purple group). Underside: with prickles. Stipules: Length: 3.5 cm, glandular. Color: RHS 146A (yellow-green group). Auricle: Shape: Lanceolate. Length: 11 mm. Width: 3 mm. Color: RHS 146A (yellow-green group). Vein Color: Color: RHS 147A (yellow-green group). Venation Pattern: Reticulate.

*Wood.*—New Wood: Color: RHS 183A (greyed-purple group). Bark: Smooth. Old Wood: Color: RHS 146B (yellow-green group). Bark: Smooth.

*Branching habit.*—Number: 3-4. Branching Dimension: Length: 35-60 cm. Diameter: 7 mm.

*Stems.*—Mature Stem: Length: 90 cm. Diameter: 1 cm. Internode Distance: 8-14 cm. The above measurements are all variable, depending on growing conditions in a season. Stem Pubescence Present: No.

*Prickles.*—Quantity: On main canes from base: None. On laterals from main canes: Few. Number per stem length: 3 per 10 cm. Form: Deep concave. Length: 4-5 mm. Color when young: RHS 59A (red-purple group). Color when mature: RHS 59A (red-purple group).

*Small prickles.*—Quantity: Main stalk: None. Laterals: None.

*Disease resistance.*—Mildew: Resistant. Blackspot: Resistant. Rust: Resistant.
*Pest resistance.*—Not tested.
*Winter hardiness.*—Not tested.
*Growing conditions.*—Normal garden conditions.

What is claimed is:

1. A new and distinct variety of rose plant of the shrub class, substantially as herein shown and described.

* * * * *

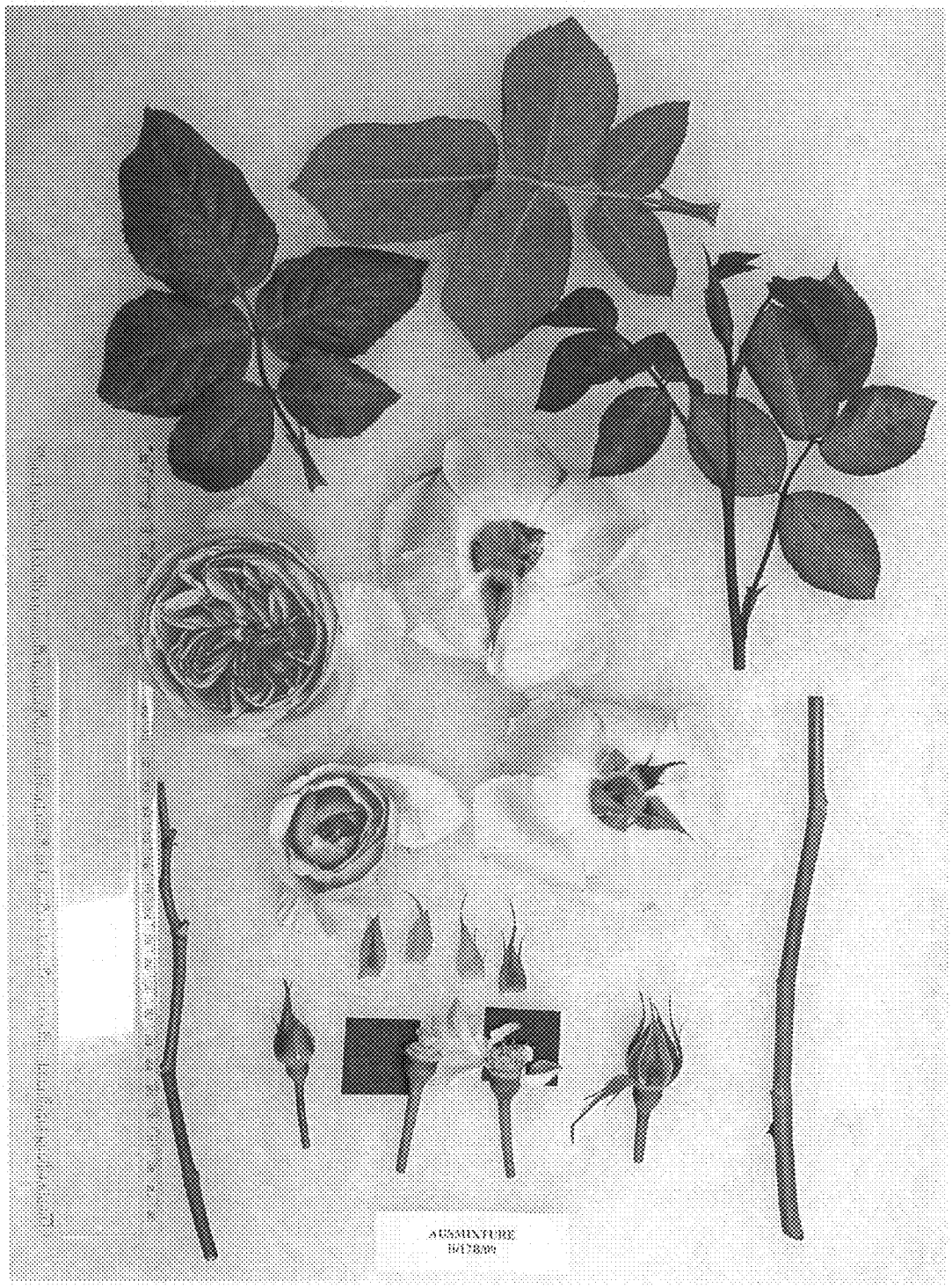
AGSMINTURE
B/2/8/09